US00PP11435P

United States Patent [19]

Zaiger et al.

[11] Patent Number: Plant 11,435

[45] Date of Patent: Jul. 4, 2000

[54] PEACH TREE 'SNOW GEM'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 09/053,122

[22] Filed: Apr. 1, 1998

[51] Int. Cl.[7] ..... A01H 5/00

[52] U.S. Cl. ..... Plt./196

[58] Field of Search ..... Plt./196, 198, 190

[56] References Cited

U.S. PATENT DOCUMENTS

P.P. 5,821 12/1986 Zaiger et al. ..... Plt./196
P.P. 8,415 10/1993 Zaiger et al. ..... Plt./196

*Primary Examiner*—Howard J. Locker
*Assistant Examiner*—Wendy A. Baker

[57] ABSTRACT

A new and distinct variety of peach tree (*Prunus persica*); its novelty consists of the following unique combination of features that are desirable in a new variety. The following features of the tree and its fruit are characterized with the tree budded on Nemaguard rootstock, grown on Hanford sandy loam soil with Storie Index rating 95, in USDA Hardiness Zone 9, near Modesto, Calif., and with standard commercial cultural fruit growing practices, such as, pruning, thinning, spraying, irrigation, and fertilization:

1. Heavy and regular production of large, white flesh fruit.
2. Fruit with good handling and shipping quality.
3. Mild, sub-acid, sweet fruit with excellent flavor and eating quality.
4. Relatively uniform size fruit throughout the tree.
5. Having a vigorous, upright growth habit.
6. Attractive fruit with a red blush over a yellowish white ground color.

1 Drawing Sheet

ORIGIN OF THE VARIETY

The present new variety was originated by us in our experimental orchard located near Modesto, Calif., as a first generation cross between two selected seedlings with field identification numbers '102ED609' (unpatented) and '105ED275' (unpatented). The maternal parent ('102ED609') was selected for a future parent in our breeding program and originated as a selected seedling from a cross between a nectarine of unknown parentage and Redwing Peach (U.S. Plant Pat. No. 621) crossed with a seedling that originated from open pollinated 'O'Henry' Peach (U.S. Plant Pat. No. 2,964) seeds. The pollen parent ('105ED275') was selected for a future parent in our breeding program and originated from a seedling selection (parentage of Red Grand Nectarine (U.S. Plant Pat. No. 1,060)) crossed with a seedling originating from a cross of 'Royal Gold' Peach (U.S. Plant Pat. No. 2,663) with 'White Lady' Peach (U.S. Plant Pat. No. 5,821). A large group of these first generation seedlings, growing on their own root, were planted and maintained by us in our experimental orchard, during which time one such seedling, which is of the present variety, exhibited the distinctive desirable fruit characteristics described above and was selected for asexual propagation and commercialization .

ASEXUAL REPRODUCTION OF THE VARIETY

The new and distinct variety of peach tree was asexually reproduced by budding to Nemaguard rootstock, the standard rootstock for peaches and nectarines in California, as performed by us in our experimental orchard located near Modesto, Calif., and shows that all characteristics of the tree and its fruit run true to the original tree and are established and transmitted through succeeding asexual propagations.

SUMMARY OF THE VARIETY

The present new and distinct variety of peach tree is of large size, vigorous, upright growth; and a productive and regular bearer of large, white flesh, freestone fruit with excellent flavor and eating quality. The fruit is further characterized by having firm flesh with good handling and shipping quality, having relatively uniform, large size fruit throughout the tree and maturing in the late maturity season, approximately 18 days after 'O'Henry' Peach (U.S. Plant Pat. No. 2,964).

DESCRIPTION OF THE PHOTOGRAPH

The accompanying photographic illustration shows typical specimens of the foliage and fruit of the present new fruit variety. The illustration shows the upper and lower surface of the leaves, an exterior and a sectional view of a fruit divided in the suture plane to reveal flesh coloration, pit cavity and a stone remaining in place. The photograph was taken shortly after being picked at maturity (shipping ripe) and the colors are as nearly true as is reasonably possible in a color representation of this type.

DESCRIPTION OF THE VARIETY

The following is a botanical description of our new and distinct variety of peach tree, its flowers, foliage and fruit are based on observations of specimens grown in our experimental orchard located near Modesto, Calif., with color terminology (except those in common terms) referenced to Reinhold Color Atlas by A. Kornerup and J. H. Wanscher.

Tree:

*Size.*—Large. Height and width are reduced to approximately 12 to 14 feet for economical harvesting of fruit.

*Vigor.*—Vigorous. Approximately 5 to 7 feet of growth in height and 4 to 5 feet of growth in width during the first growing season. During the first dormant season, the primary scaffolds are selected and the tree is pruned to approximately 4 to 5 feet in height and 3 to 4 feet in width. Height and width vary with type and depth of soil, cultural practices and climatic conditions.

*Density.*—Medium dense. Usually pruned to vase shape to allow more air and sunlight to the center of tree for enhanced color and brix of fruit.

*Productivity.*—Productive. Fruit set is usually 2 or more times the desired fruit for normal tree crop load and must be thinned and properly spaced to develop into desirable market fruit size.

*Growth.*—Upright. Under normal fruit cultural practices, the trees are pruned to a height of 12 to 14 feet for economical fruit harvesting. If the tree is left unpruned it would grow considerably larger in height and width.

*Hardiness.*—Winter chilling requirement is approximately 850 hours below 45° F. Hardiness tested in USDA Hardiness Zone 9.

*Bearing.*—Regular.

Trunk:

*Size.*—Medium to large. Measured 19½ inches in circumference at 14 inches above ground, on a 9 year old tree.

*Texture.*—Medium shaggy.

*Color.*—Brown to dark brown (5-E-4) to (5-F-5). Varies with age of tree.

Branches:

*Size.*—Medium. Circumference measured 3 feet above ground, varied from 6½ to 9¼ inches. Scaffolds were selected with wide angle crotch to carry heavy crop load and open center of tree sunlight and air circulation.

*Surface.*—Smooth to medium rough, varies with age of growth.

*Lenticels.*—Few in number. Small size. Within a 4 square inch section the number varied from 20 to 24. Average length 3/32 inch. Average width 1/32 inch.

*Color.*—Light brown to grayish brown (5-E-6) to (5-E-8). Varies with age of growth.

Leaves:

*Size.*—Large. Average length — 6½ inches. Average width — 1½ inches.

*Form.*—Lanceolate, pointed.

*Margin.*—Crenate.

*Texture.*—Smooth.

*Thickness.*—Medium.

*Petiole.*—Medium length. Medium Thickness.

*Glands.*—Reniform. Number varies from 1 to 5. Average number 3. Positioned on base of leaf blade and upper portion of petiole. Color — yellowish green to light green (30-B-8) to (30-C-8).

*Color.*—Upper surface — green to dark green (28-F-7) to (28-F-8). Lower Surface — light green to green (28-E-7) to (28-E-8).

Flower buds:

*Size.*—Medium to large.

*Form.*—Plump.

*Length.*—Medium.

*Pubescence.*—Pubescent.

Flowers:

*Size.*—Large, showy. Average height 51/64 inch. Average diameter 1 51/64 inches. Petal shape nearly orbicular, slightly elongated, narrows at point of attachment.

*Aroma.*—Very slight fragrance.

*Blooming period.*—Date of first bloom: Mar. 3, 1996. Date of last bloom: Mar. 9, 1996. Varies slightly with climatic conditions.

*Pollen.*—Present, self-fertile.

*Color.*—Pink to light pink (12-A-2) to (12-A-3). Color fades with age of flower.

Fruit:

*Maturity when described.*—Firm ripe.

*Date of first picking.*—Aug. 16, 1996.

*Date of last picking.*—Aug. 22, 1996. Varies slightly with climatic conditions.

*Size.*—Large, relatively uniform. Average diameter axially 3 inches. Average transversely in suture plane 3¼ inches. Average weight 255 grams. Average weight varies slightly with fertility of the soil, amount of thinning and climatic conditions.

*Form.*—Nearly globose, slightly flattened at base.

*Suture.*—Shallow, extends from base to slightly beyond apex.

*Ventral surface.*—Nearly rounded, some fruit slightly lipped.

*Cavity.*—Rounded to slightly elongated in suture plane. Average depth — ⅜ inch. Average breadth — ¾ inch.

*Base.*—Retuse.

*Apex.*—Usually rounded.

Skin:

*Thickness.*—Medium.

*Texture.*—Medium, tenacious to flesh.

*Tendency to crack.*—None.

*Down.*—Moderate, medium length.

*Color.*—Yellowish white to cream ground color (4-A-2) to (4-A-3). Partially overspread with red to turkish red (10-C-7) to (10-C-8). Slightly darker with amount of exposure to direct sunlight.

Flesh:

*Ripens.*—Evenly.

*Texture.*—Firm.

*Fibers.*—Few, small, tender.

*Aroma.*—Slight to moderate. Varies slightly with degree of maturity when harvested.

*Juice.*—Moderate. Mild, sweet, enhances flavor.

*Amygdalin.*—Undetected.

*Flavor.*—Excellent.

*Brix.*—Average 11.4°. Varies slightly with weather conditions during fruit maturity and number of fruit on tree.

*Eating quality.*—Excellent.

*Color.*—White to pinkish white (7-A-1) to (7-A-2). Pit Cavity — red to turkish red (10-B-8) to (10-C-8). Slight bleeding of red into flesh from pit cavity.

Stone:

*Size.*—Large. Average length — 1½ inches. Average width — 1 3/16 inches. Average thickness — ⅞ inch.

*Type.*—Freestone.

*Form.*—Obovate.

*Base.*—Straight.

*Apex.*—Cuspidate.

*Sides.*—Usually unequal, varies from equal to unequal.

*Surface.*—Irregularly furrowed toward apex, pitted toward base, pit cavities vary from round to elongated.

*Ridges.*—Narrow, vary from dull to sharp.

*Tendency to split.*—None.

*Color.*—Reddish brown to brown (6-E-5) to (7-E-5).

Use: Dessert.

*Market.*—local and long distance.

Keeping quality: Good. Fruit stored from 3 weeks at 38° to 42° F., showed no internal browning or wooliness of flesh.

Shipping quality: Good. Fruit showed minimal scarring or bruising of skin or flesh during packing and shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed.

The present new variety of peach tree, its flowers, foliage and fruit herein described may vary in slight detail to climate, soil conditions and cultural practices under which the variety may be grown, the present botanical description is that of the variety grown under the ecological conditions prevailing near Modesto, Calif.

We claim:

1. A new and distinct variety of peach tree, substantially as illustrated and described, characterized by its large size, vigorous, upright growth and being a productive and regular bearer of large size, firm, white flesh, freestone fruit and good handling and shipping quality; the fruit is further characterized by being relatively uniform in size throughout the tree, having excellent flavor and eating quality and maturing in the late maturity season, approximately 18 days later than 'O'Henry' Peach (U.S. Plant Pat. No. 2,964).

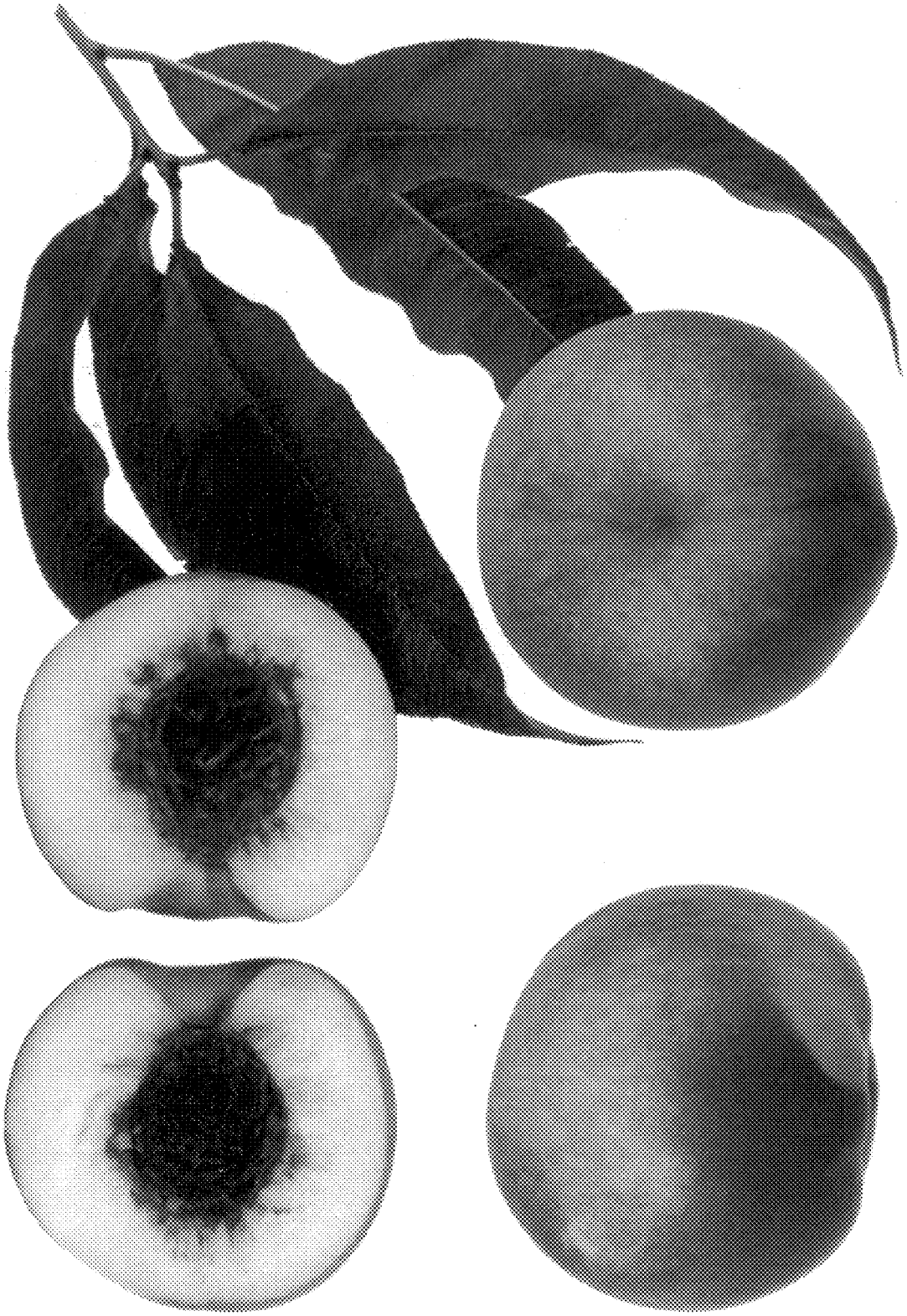

* * * * *